United States Patent [19]

Gousetis et al.

[11] Patent Number: 4,827,008

[45] Date of Patent: May 2, 1989

[54] PREPARATION OF ALKOXYSILANES CONTAINING A LOW LEVEL OF CHLORINE COMPOUNDS

[75] Inventors: Charalampos Gousetis; Knut Oppenlaender, both of Ludwigshafen; Gert Liebold, Edingen-Neckarhausen; Guenter Frey, Dannstadt-Schauernheim, all of Fed. Rep. of Germany

[73] Assignee: BASF Aktiengesellschaft, Ludwigshafen, Fed. Rep. of Germany

[21] Appl. No.: 165,493

[22] Filed: Mar. 8, 1988

[30] Foreign Application Priority Data

Mar. 14, 1987 [DE] Fed. Rep. of Germany ....... 3708293

[51] Int. Cl.$^4$ .............................. C07F 7/08; C07F 7/18
[52] U.S. Cl. ..................................... 556/466; 556/443; 556/444; 556/471
[58] Field of Search ................. 556/471, 443, 444, 466

[56] References Cited

U.S. PATENT DOCUMENTS

| | | | |
|---|---|---|---|
| 2,484,394 | 10/1949 | Van Zwet | 556/471 |
| 2,814,635 | 11/1957 | Scheel et al. | 556/471 |
| 3,985,781 | 10/1976 | Kotzsch et al. | 260/448.8 R |
| 3,994,948 | 11/1976 | Jayne et al. | 260/448.8 R |
| 4,173,576 | 11/1979 | Seiler et al. | 556/471 |
| 4,228,092 | 10/1980 | Kotzsch et al. | 556/422 |
| 4,467,105 | 8/1984 | Kotzsch et al. | 556/444 |
| 4,697,027 | 9/1987 | Sugihara et al. | 556/466 |

FOREIGN PATENT DOCUMENTS

| | | |
|---|---|---|
| 2445552 | 5/1975 | Fed. Rep. of Germany ... 556/471 UX |
| 2609767 | 4/1977 | Fed. Rep. of Germany ...... 556/471 |
| 2409731 | 5/1983 | Fed. Rep. of Germany ... 556/471 UX |
| 2800017 | 5/1983 | Fed. Rep. of Germany ... 556/471 UX |
| 3138835 | 12/1986 | Fed. Rep. of Germany ... 556/471 UX |

*Primary Examiner*—Paul F. Shaver
*Attorney, Agent, or Firm*—Keil & Weinkauf

[57] ABSTRACT

Alkoxysilanes containing low levels of chlorine compounds are prepared by stepwise etherification of chlorosilanes with alcohols in liquid phase and removal of the resulting hydrogen chloride by reacting the alkoxysilane obtained, which still contains a small amount of chlorine compound, with a metal alkoxide in an amount which corresponds to a small stoichiometric excess based on the proportion of chlorine compound, and freeing the reaction product from the resulting salt.

5 Claims, No Drawings

PREPARATION OF ALKOXYSILANES CONTAINING A LOW LEVEL OF CHLORINE COMPOUNDS

The present invention relates to a process for preparing alkoxysilanes containing a low level of chlorine compound by treating the reaction product of chlorosilanes with alcohols with small amounts of metal alkoxides.

The preparation of alkoxysilanes, in particular those which can be added to brake fluids, is described in detail in German Patents 2,409,731, 2,445,552 and 3,138,835. In this prior art, the starting point is always a chlorosilane which is either directly reacted with the desired alcohol or first converted into a low molecular weight ether which is transetherified with higher alcohols. This reaction gives rise to hydrogen chloride which can react further with excess alcohol to form alkyl chlorides and water. The water formed can in turn initiate polycondensation reactions which can lead to substantial reductions in yield (cf. Kirk-Othmer's Encyclopedia of Chemical Technology, 3rd ed. vol. 20, p. 916).

To avoid the secondary reactions caused by the HCl, there are prior art processes which make it possible to remove the bulk of the HCl during the reaction. To this end it is proposed for example in German Patent 2,409,731 that the reaction be carried out in stages and with the alcohol being introduced beneath the surface of the liquid phase. A similar stagewise approach is proposed in DE-C2-2,800,017.

Despite these measures it is unavoidable that the reaction products still contain undesirable organic chlorine compounds. This is also true of the products of DE-C2-3,138,835, since the starting material for the low molecular weight alkoxysilanes is contaminated with organic chlorine compounds from their synthesis. For this reason it has even been suggested that products having a low chlorine content be obtained by performing the reaction in the presence of stoichiometric amounts of tertiary bases, such as pyridine, N,N-dimethylaniline or triethylamine (cf. C. Eaborn, Organosilicon Compounds, 1960 N.Y., Academic Press, p. 288). It is true that by adding these amines it is possible to reduce the level of chlorine compounds substantially, but the use of stoichiometric amounts of amines is very expensive. Similarly, the aforementioned approach to removing HCl by appropriate process management leads to products which need to be purified by distillation to reduce the chlorine content.

It is an object of the present invention to propose a process which makes it possible to prepare alkoxysilanes containing very low levels of chlorine compounds without additional expensive measures and without using substantial amounts of auxiliary products.

We have found that this object is achieved with a process for preparing an alkoxysilane containing a low level of chlorine compound by stepwise etherification of a chlorosilane with an alcohol in liquid phase and removal of the resulting hydrogen chloride, which comprises reacting the alkoxysilane obtained, which still contains a small amount of chlorine compound, with a metal alkoxide in an amount which corresponds to a small stoichiometric excess based on the proportion of chlorine compound, and freeing the reaction product from the resulting salt.

Alkoxysilanes which can be prepared according to the invention include for example those of the formula I

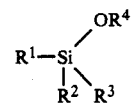

where $R^1$, $R^2$ and $R^3$ are each aliphatic, araliphatic or aromatic radicals of 1 to 20 carbon atoms, or $OR^4$, $R^1$ can also be hydrogen, and $OR^4$ is the radical of a monohydric alcohol of 1 to 20 carbon atoms, prepared by reacting chlorosilanes of the formula II

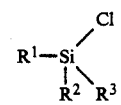

with alkanols of the formula III

     III where $R^1$, $R^2$, $R^3$ and $R^4$ each have the abovementioned meanings, $R^1$, $R^2$ and $R^3$ can each further be chlorine and $R^1$ can also be hydrogen, and treating the reaction product with metal alkoxides.

The preferred alkoxysilanes according to this invention are those where the alcohol $HOR^4$ is a polyglycol monoether of the formula IV

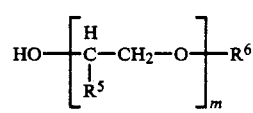

where $R^5$ is hydrogen or methyl, $R^6$ is alkyl of 1 to 8 carbon atoms, and m is an integer from 1 to 4.

In particular, the invention provides alkoxysilanes of the formula V

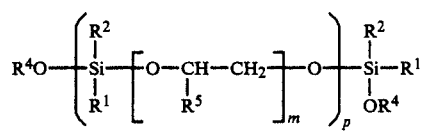

where $R^1$ and $R^2$ are each alkyl of 1 to 20 carbon atoms, $R^2$ can also be $OR^4$, and $OR^4$ is the radical of the formula VI

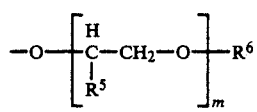

where $R^5$ is hydrogen or methyl, $R^6$ is alkyl of 1 to 8 carbon atoms, m is an integer from 1 to 4, p is an integer from 1 to 10, which contain very low levels of chlorine compound Suitable metal alkoxides for the reaction according to the invention are in general alkali metal and alkaline earth metal alkoxides. Suitable are in particular potassium alkoxides and preferably sodium alkoxides. In the alkoxides, the alkoxide moiety is advantageously derived from the alcohol corresponding to the radicals already bonded to the ether oxygen. The alkoxides are obtained in a conventional manner, for example as described in detail in Ullmann's Enzyklopädie der Technischen Chemie, 4th ed., vol. 7, p. 220, which is hereby incorporated herein by reference.

For the reaction according to the invention, the alkoxide is used in such an amount that a small excess, for example a 10-30% excess, is present relative to the stoichiometrically required amount.

The reaction for reducing the level of chlorine compounds is advantageously carried out in detail by reacting the etherification product with or without a solvent, such as toluene or xylene, at from 80° to 200° C., preferably at from 100° to 150° C. with the metal alkoxide, in particular sodium alkoxide, for 5–30 hours. The reaction product is then removed by filtration from the relatively small amount of metal chloride precipitate and is used without further purification, if necessary after removal of the solvent. The addition of a solvent is advantageous when the chloride salt is more soluble in the product than in the solvent.

The chlorine content of alkoxysilanes which after the direct etherification reaction still contain chlorine compounds is customarily within the range from 0.1 to 1% by weight. By using the process according to the invention it is possible to reduce this chlorine content to 0.001–0.02% by weight. This result is surprising because the addition of tertiary amines such as pyridine, N,N-dimethylaniline or triethylamine under otherwise comparable reaction conditions and in the presence of the corresponding alcohol (III, IV) converts only a small fraction (about 5%) of the chlorine still present into amine hydrochlorides.

The alkoxysilanes which can be subjected to the aftertreatment of the invention are obtainable in a conventional manner (cf. Emblem and Hargreaves, J. Inorg. Nucl. Chem. 30 (1968), 721) starting from chlorosilanes such as methyltrichlorosilane, methyldichlorosilane, dimethylchlorosilane, trimethylchlorosilane, ethyltrichlorosilane, ethyldichlorosilane, propyltrichlorosilane, butyltrichlorosilane, amyltrichlorosilane, octyltrichlorosilane, 2-ethyltrichlorosilane, dodecyltrichlorosilane, vinyltrichlorosilane, vinyldimethylchlorosilane, allyltrichlorosilane, 3-allyloxypropyltrichlorosilane, benzyltrichlorosilane, benzylmethyldichlorosilane, 2-phenylethyltrichlorosilane, phenylmethyldichlorosilane or diphenyldichlorosilane or tetrachlorosilane. Examples of alcoholic components are monohydric primary aliphatic alcohols of 1 to 20 carbon atoms or monoethers of polyalkylene glycols, such as methylglycol, ethylglycol, propylglycol or butylglycol, or di-, tri- or tetraethylene glycol monomethyl, monoethyl, monopropyl or monobutyl ether. The alcohol component may also comprise dihydric aliphatic alcohols such as ethylene glycol, 1,2-propylene glycol, 1,2-butylene glycol and other diols of 3 to 12 carbon atoms in a straight or branched chain. Also possible are polyalkylene glycols from 2 to 4 molecules of ethylene oxide or propylene oxide and also polyhydric alcohols such as trimethylolpropane and pentaerythritol. The products may contain identical or different alkoxies.

The use of polyols makes it possible to synthesize products having a plurality of Si atoms in the molecule. For instance, compounds of the abovementioned formula V can be obtained. In the case of polychlorosilanes, all the chlorine atoms are substituted in succession at continuously rising temperatures. For this reason the reaction with the metal alkoxide is not carried out until the chlorine content of the reaction mixture shows no further significant decrease despite elevated temperatures and continued stirring; this is usually the case after about 20 hours and a reaction temperature of 200° C.

EXAMPLE

The process according to the invention will be illustrated in the preparation of alkoxysilane VIII

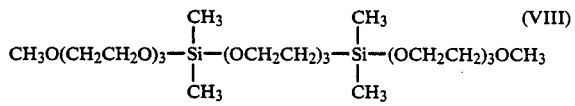

This product and its condensation products as described in DE 3,138,835 are suitable for use as hydraulic fluids (cf. GB 1,480,738).

500 g (3.88 mol) of dimethyldichlorosilane are introduced at 50°–60° C., and 291 g (1.94 mol) of triethylene glycol are metered in over 70 minutes through a tube dipping beneath the surface of the liquid. The resulting HCl is expelled from the reaction mixture by means of a dry $N_2$ stream. The mixture is stirred at 80° C. for a further 60 minutes, and a start is then made on adding 699 g (4.26 mol) of methyltriglycol as described above. The addition is complete after 150 minutes. The temperature is then raised to 180° C., and stirring is continued at that temperature for 20 hours. The product (1,150 g) still contains 0.44% of Cl.

1,100 g of this product are then introduced at 110°–120° C. in 1,130 g of toluene, and 30.4 g (0.164 mol) of $CH_3OCH_2CH_2OCH_2CH_2OCH_2CH_2ONa$ (20 mol % excess based on 1 mol of Cl in product) are added dropwise. Stirring under reflux is then continued for a further 8 hours, which is followed by cooling to room temperature and removal of the precipitate by filtration. Volatiles are then removed at up to 120° C./0.3 mbar.

Yield: 995 g of (VIII) including small amounts of the condensation product of the formula (V) where $R^1=R^2=CH_3$, $R^4=CH_3OCH_2CH_2OCH_2CH_2OCH_2CH_2-$, $R^5=H$, $m=3, 1<p<10$.

The end product contains 0.016% of Cl. By comparison, (VIII) prepared as described in GB 1,480,738 (Example 1) using stoichiometric amounts of pyridine contains 0.03% of Cl.

The product has the following properties:
C 48.5%; H 8.4%; Si 7.6%.
Viscosity at.
−40° C.: 890 $mm^2\,sec^{-1}$
+100° C.: 2.7 $mm^2\,sec^{-1}$
Boiling point: 293° C.
Wet boiling point (by SAE J 1703 and FMV SS116): 234° C.

We claim:

1. A process for preparing an alkoxysilane containing from about 0.001 to 0.02% by weight of organic chlorine compound by stepwise etherification of a chlorosilane with an alcohol in liquid phase and removal of the resulting hydrogen chloride, which comprises reacting the alkoxysilane obtained, which still contains a small amount of chlorine compound, with a metal alkoxide in an amount which corresponds to a small stoichiometric excess based on the proportion of chlorine compound, and freeing the reaction product from the resulting salt.

2. A process as defined in claim 1, for preparing an alkoxysilane of the formula I

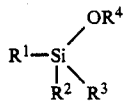    I where $R^1$, $R^2$ and $R^3$ are each aliphatic, araliphatic or aromatic radicals of 1 to 20 carbons atoms or $OR^4$, $R^1$ can also be hydrogen, and $OR^4$ is the radical of a monohydric alcohol of 1 to 20 carbon atoms, by reacting a chlorosilane of the formula II

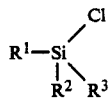    II with an alkanol of the formula III

HO—$R^4$    III where $R^1$, $R^2$, $R^3$ and $R^4$ each have the abovementioned meanings, $R^1$, $R^2$ and $R^3$ can each further be chlorine and $R^1$ can also be hydrogen, and treating the reaction product with a metal alkoxide.

3. A process as defined in claim 2, wherein the alcohol HO—$R^4$ is a polyglycol monoether of the formula IV

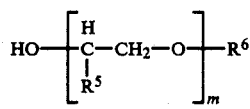    IV where $R^5$ is hydrogen or methyl, $R^6$ is alkyl of 1 to 8 carbon atoms and m is an integer from 1 to 4.

4. A process as defined in claim 1, for preparing an alkoxysilane of the formula V

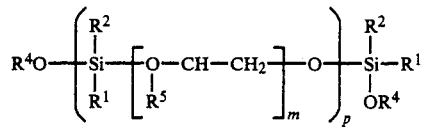    V where $R^1$ and $R^2$ are each alkyl of 1 to 20 carbon atoms, $R^2$ can also be $OR^4$, and $OR^4$ is the radical of the formula

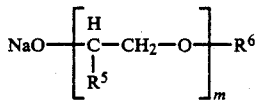    VI

VI.

where $R^5$ is hydrogen or methyl, $R^6$ is alkyl of 1 to 8 carbon atoms, m is an integer from 1 to 4, and p is an integer from 1 to 10.

5. A process as defined in claim 1, wherein the metal alkoxide used is a sodium alkoxide of the formula VII $$NaO\left[\begin{array}{c}H\\|\\C-CH_2-O\\|\\R^5\end{array}\right]_m R^6 \quad VII$$

where $R^5$, $R^6$ and m are as defined in claim 4.

* * * * *